(12) United States Patent
Griffith et al.

(10) Patent No.: US 12,426,893 B2
(45) Date of Patent: Sep. 30, 2025

(54) BILATERAL REVERSIBLE VENOUS TOURNIQUET BANDS

(71) Applicant: IPC, LLC, Lakeville, MN (US)

(72) Inventors: Martin J. Griffith, Prior Lake, MN (US); Ronald E. Griffith, Lakeville, MN (US); Stephen L. Griffith, Lakeville, MN (US)

(73) Assignee: IPC, LLC

( * ) Notice: Subject to any disclaimer, the term of this patent is extended or adjusted under 35 U.S.C. 154(b) by 291 days.

(21) Appl. No.: 18/121,606

(22) Filed: Mar. 15, 2023

(65) Prior Publication Data
US 2023/0218304 A1  Jul. 13, 2023

Related U.S. Application Data

(63) Continuation-in-part of application No. 17/101,003, filed on Nov. 23, 2020, now abandoned.

(51) Int. Cl.
| | | |
|---|---|---|
| *A61B 17/132* | (2006.01) | |
| *A61B 90/92* | (2016.01) | |
| *A61B 17/00* | (2006.01) | |
| *A61B 90/00* | (2016.01) | |

(52) U.S. Cl.
CPC ......... *A61B 17/1322* (2013.01); *A61B 90/92* (2016.02); *A61B 2017/0023* (2013.01); *A61B 2017/00845* (2013.01); *A61B 2017/00858* (2013.01); *A61B 2017/00955* (2013.01); *A61B 2090/3941* (2016.02)

(58) Field of Classification Search
CPC ... A61B 17/132; A61B 17/1322; A61B 90/92; A61B 2017/0023; A61B 2017/00845; A61B 2017/00858; A61B 2017/00861; A61B 2017/00955; A61B 2090/3941
See application file for complete search history.

*Primary Examiner* — Ryan J. Severson
(74) *Attorney, Agent, or Firm* — Gearhart Law LLC

(57) ABSTRACT

Disclosed herein are embodiments for a bilateral reversible disposable tourniquet band. The band tourniquet comprises an elongated member having a flat structure made of a thermoplastic elastomer material. The band has a first surface having a smooth texture, and a second surface having a non-smooth texture comprising a knurled pattern. The elongated member may have a thickness between 0.5 mm and 2 mm.

17 Claims, 5 Drawing Sheets

BILATERAL REVERSIBLE VENOUS TOURNIQUET BANDS

CROSS-REFERENCE TO RELATED APPLICATIONS SECTION

This application is a Continuation In Part Application entitled, "BILATERAL REVERSIBLE VENOUS TOURNIQUET BANDS", which claims priority to co-pending U.S. Non-Provisional patent application Ser. No. 17/101,003 filed Nov. 23, 2020, entitled, "BILATERAL REVERSIBLE VENOUS TOURNIQUET BANDS", the entire contents of which are hereby incorporated by reference in their entirety.

FIELD OF THE EMBODIMENTS

The field of the invention and its embodiments generally relate to disposable venous tourniquet bands.

BACKGROUND OF THE EMBODIMENTS

Healthcare professionals use disposable venous tourniquet bands to perform venipunctures and other procedures involving intravenous access to veins. In general, a tourniquet is used to apply pressure to a limb or extremity to limit blood flow. Disposable tourniquets are typically used for drawing blood from patients in a healthcare setting. Using the disposable variety of tourniquets is more hygienic and convenient than having to sterilize reusable tourniquets.

However, current disposable venous tourniquet bands are sometimes unsuitable or unpleasant for patients and healthcare providers due to, for example, physical limitations, skin conditions, technical preferences, etc.

SUMMARY OF THE EMBODIMENTS

In accordance with the principles of the present invention, a bilateral reversible venous tourniquet band having a knurled crossed pattern with a phosphorescence material, and which also includes improvements that overcome the limitations of prior bilateral reversible venous tourniquet bands, is now met by a new, useful, and non-obvious invention.

In some aspects, the techniques described herein relate to a bilateral reversible disposable tourniquet band including: an elongated member having a flat structure, the elongated member included of a thermoplastic elastomer material, the elongated member including: a first surface having a smooth texture; and a second surface having a non-smooth texture including a knurled crossed pattern, the second surface being opposite the first surface, the knurled crossed pattern including a pattern of protrusions and recesses including rows of repeating pyramidal shapes having a tapered configuration, at least one protrusion of the pattern of protrusions having a phosphorescent material.

In some aspects, the techniques described herein relate to a bilateral reversible disposable tourniquet band, wherein the knurled crossed pattern includes a crossed pattern with a pitch between protrusions of between 0.1 mm and 1 mm.

In some aspects, the techniques described herein relate to a bilateral reversible disposable tourniquet band, wherein the bilateral reversible disposable tourniquet band is packaged as a multiple tourniquet band reel.

In some aspects, the techniques described herein relate to a bilateral reversible disposable tourniquet band, wherein the bilateral reversible disposable tourniquet band is packaged flat for transportation in a box.

In some aspects, the techniques described herein relate to a bilateral reversible disposable tourniquet band, wherein the bilateral reversible disposable tourniquet band has a length of approximately 18 inches.

In some aspects, the techniques described herein relate to a bilateral reversible disposable tourniquet band, wherein the bilateral reversible disposable tourniquet band includes a colorant added to the thermoplastic elastomer material.

In some aspects, the techniques described herein relate to a bilateral reversible disposable tourniquet band, wherein the phosphorescent material is integrally formed within the knurled crossed pattern.

In some aspects, the techniques described herein relate to a bilateral reversible disposable tourniquet band, wherein the phosphorescent material overlays a distal portion of at least one protrusion of the pattern of protrusions of the knurled crossed pattern.

In some aspects, the techniques described herein relate to a bilateral reversible disposable tourniquet band, wherein the phosphorescent material overlays the recesses of the knurled crossed pattern.

In some aspects, the techniques described herein relate to a bilateral reversible disposable tourniquet band, wherein the phosphorescent material does not overlay a distal portion of at least one protrusion of the pattern of protrusions of the knurled crossed pattern.

In some aspects, the techniques described herein relate to a bilateral reversible disposable tourniquet band including: an elongated member having a flat structure, the elongated member included of a thermoplastic elastomer material, the elongated member including: a first surface having a smooth texture, and a second surface, at least a portion of the second surface having a non-smooth texture including a knurled crossed pattern, the second surface being located opposite the first surface, the knurled crossed pattern including a pattern of protrusions including rows of repeating pyramidal shapes having a tapered configuration, a first protrusion of the pattern of protrusions is oriented adjacent to a second protrusion thereby forming a recess, at least a portion of the knurled crossed pattern being a phosphorescent material.

In some aspects, the techniques described herein relate to a bilateral reversible disposable tourniquet band, wherein the knurled crossed pattern includes a pitch between protrusions of between 0.1 mm and 1 mm.

In some aspects, the techniques described herein relate to a bilateral reversible disposable tourniquet band, wherein the phosphorescent material is integrally formed within the knurled crossed pattern.

In some aspects, the techniques described herein relate to a bilateral reversible disposable tourniquet band, wherein the phosphorescent material overlays a tip of a first protrusion of the pattern of protrusions of the knurled crossed pattern.

In some aspects, the techniques described herein relate to a bilateral reversible disposable tourniquet band, wherein the phosphorescent material overlays the recess of the knurled crossed pattern.

In some aspects, the techniques described herein relate to a bilateral reversible disposable tourniquet band, wherein the bilateral reversible disposable tourniquet band includes a colorant added to the thermoplastic elastomer material.

Disposable tourniquets are used in low light locations such as intensive care units and accident scenes. Because of the low light conditions combined with the high stress and rushed conditions when using a disposable tourniquet, there is a significant likelihood that healthcare personnel will forget to remove the tourniquet after a medical procedure. If a tourniquet is forgotten on a patient, there is a chance of permanent damage to the body part or death of the patient.

Due to the inherent problems with the related art, there is a need for a new and improved glow-in-the-dark tourniquet system for providing a tourniquet that remains visible in low-light conditions.

Another object of the present invention is to provide a glow-in-the-dark tourniquet that decreases the likelihood that the tourniquet will be gathered with the bed coverings or gowns and put through the washing machine which can disintegrate causing problems in the washing equipment.

The elongated strip includes a colorant (e.g., color masterbatch, colored pellets, colored compounds, colored pigments, etc.) that may be dispersed throughout the entire elongated strip or forming a pattern. A phosphorescent component is added to the elongated strip to provide a visual reminder to medical personnel in reduced lighting conditions to remove the tourniquet (e.g., nighttime, mines, etc.). The phosphorescent component may be comprised of phosphorescent inks, phosphorescent masterbatch, phosphorescent pellets, phosphorescent compounds or phosphorescent pigments. The phosphorescent component may be added throughout the entire elongated strip or only in certain portions of the elongated strip to form patterns such as stripes, symbols and; or words.

The elongated member further preferably includes a colorant added to the base material to provide any desired color (e.g., white, violet, blue, green, yellow, red, orange, pink). One or more colors may be used within the elongated member (e.g., one color for the main body and another color for the indicia). The color may be evenly dispersed throughout the elongated member or the color may be used in the elongated member to form a pattern such as symbols, shapes, stripes, characters, anchor words.

Examples of suitable colorants include, but are not limited to, color masterbatch, colored pellets, colored compounds, colored pigments. The colorants may be a masterbatch colorants that is a solid or a liquid additive used for coloring polymers (color masterbatch) such as plastics or imparting other properties to plastics (additive masterbatch). Instead of a colorant added to the base material, the colorant may be printed on the surface of the elongated member such as by using colored inks.

The elongated member includes a phosphorescent material (i.e., glow-in-the-dark material) either integrally formed within the elongated member during manufacture and/or attached to the surface of the elongated member as a layer of phosphorescent material. The phosphorescent material may be evenly distributed throughout the elongated member (e.g., completely through the entire elongated member) or the phosphorescent material may be used in the elongated member to form a visual indicia such as symbols, shapes, patterns, stripes, characters or words. The phosphorescent material is any material that shows an afterglow in darkened light conditions after being charged by a light source (e.g. sun, building lights). Typically, phosphorescent materials continue to emit an afterglow several hours after exposure to the light source has ceased.

The elongated member may include any type of phosphorescent (i.e., glow-in-the-dark) component that is added to and mixed with the base material and the colorant of the elongated member such as, but not limited to, phosphorescent masterbatch (e.g., polymer additive), additive masterbatch, phosphorescent pellets, phosphorescent compounds, and phosphorescent pigments. The phosphorescent component/material is added to the base material during manufacturing and production of the elongated member. Examples of suitable phosphorescent materials include, but are not limited to, phosphorescent pigments based on zinc sulfide (ZnS), radioisotopes or strontium oxide aluminate. The phosphorescent material may be comprised of any color (lighted and afterglow) such as, but not limited to, white, violet, blue, green, yellow, red, orange, pink.

The phosphorescent material may also be printed on the surfaces of the elongated member such as by using a phosphorescent ink. The printing of the phosphorescent material may be evenly layered throughout the surface of the elongated member or in a manner that forms symbols, characters, one or more words, shapes, stripes, patterns within the surface of the elongated member.

BRIEF DESCRIPTION OF THE DRAWINGS

The accompanying drawings are incorporated herein and form a part of the specification.

DESCRIPTION OF THE PREFERRED EMBODIMENTS

Figure 1:
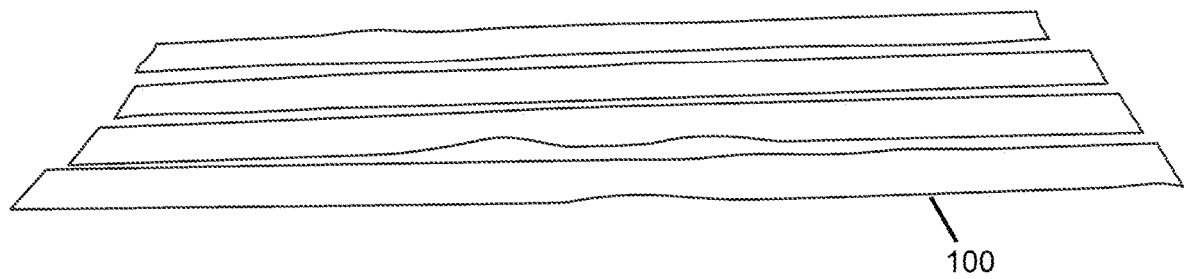
FIG. 1 illustrates a bilateral reversible disposable venous tourniquet band with textured and smooth sides, according to an example embodiment.

The preferred embodiments of the present invention will now be described with reference to the drawings. Identical elements in the various figures may be identified with the same reference numerals. Reference will now be made in detail to each embodiment of the present invention. Such embodiments are provided by way of explanation of the present invention, which is not intended to be limited thereto. In fact, those of ordinary skill in the art may appreciate upon reading the present specification and viewing the present drawings that various modifications and variations can be made thereto.

As used herein, the singular forms "a," "an," and "the," are intended to include the plural forms as well, unless the context clearly indicates otherwise.

The phrase "and/or," as used herein in the specification and in the claims, should be understood to mean "either or both" of the elements so conjoined, i.e., elements that are conjunctively present in some cases and disjunctively present in other cases. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

Provided herein are embodiments for a bilateral reversible disposable venous tourniquet band with textured and smooth sides. Previous disposable venous tourniquet bands do not allow for accommodation based on possible physical requirements or limitations of patient skin as well as to provide for various degrees of relief and well-being and/or preference.

Embodiments of the bilateral reversible venous tourniquet band w healthcare professionals to perform venipunctures and other procedures involving intravenous access to veins. The new tourniquet system provides options not previously available to the healthcare professional in one holistic system. Namely, the system may be used with the untextured/smooth side in contact with a patient's epidermis, or alternatively, as the situation may dictate, the band can be used with the textured side placed against the patient's skin.

Figure 2:
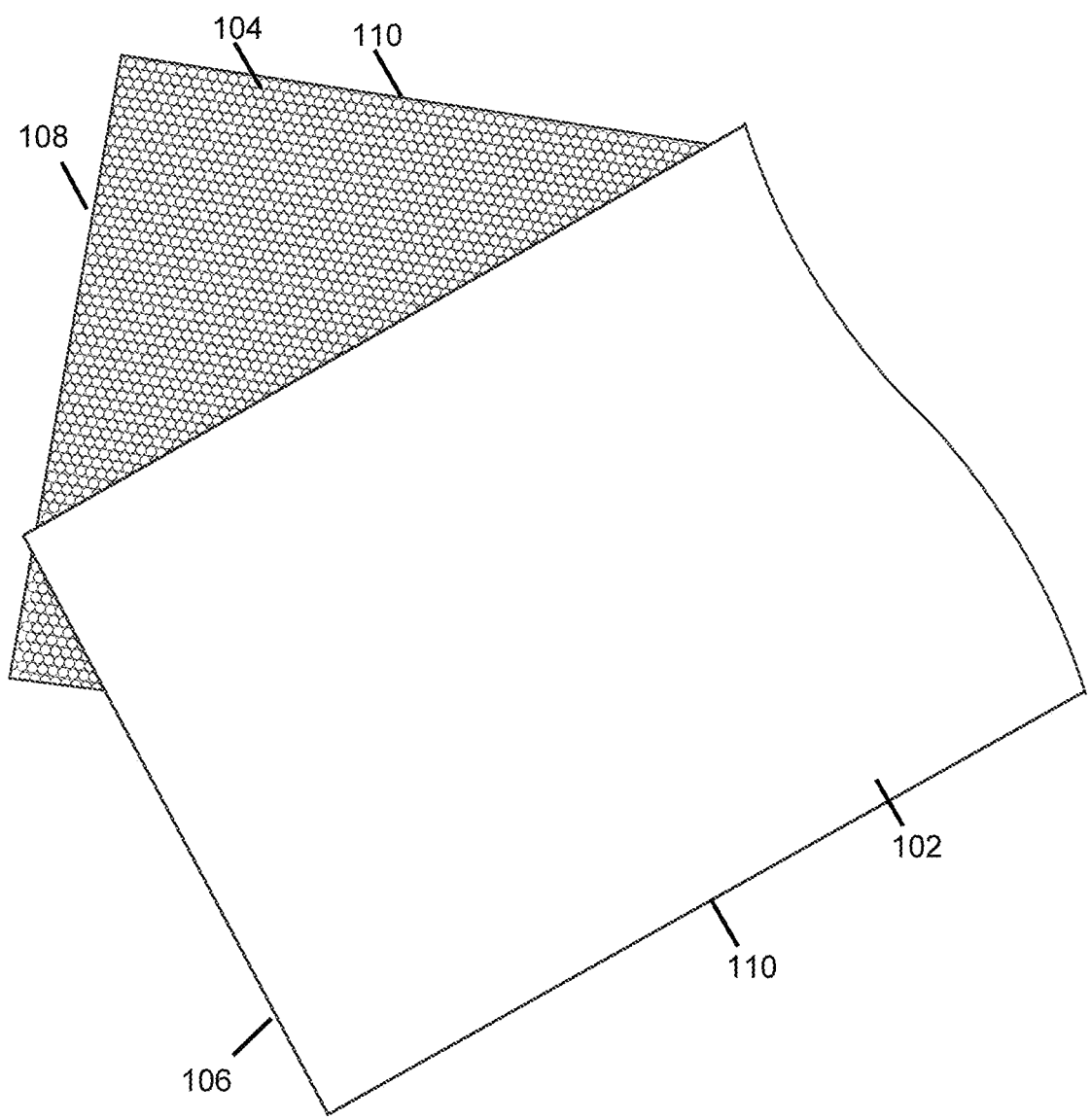
FIG. 2 illustrates a close-up view of a bilateral reversible disposable venous tourniquet band with textured and smooth sides, according to an example embodiment.

FIGS. 1 and 2 illustrate a bilateral reversible disposable tourniquet band 100, according to an example embodiment. Bilateral reversible venous tourniquet band 100 is comprised of an elongated member forming a disposable venous tourniquet having an outer surface 102, an inner surface 104 opposite of the outer surface, a first end 106 and a second end 108 opposite of the first end. The elongated member is comprised of a flat structure that has a width, a length and a thickness that may vary. The elongated member may be comprised of a flexible and elastic base material such as a thermoplastic elastomer. The elongated member may be comprised of an elastic material to allow for resilient stretching of the elongated strip. The elongated member may be comprised of a disposable material.

Regardless of the structure of the elongated member, the elongated member preferably includes a first end 106 and a second end 108 opposite of the first end as illustrated in FIG. 2. The elongated member further includes a first surface 102 (e.g., exterior surface) and a second surface 104 (e.g., interior surface) opposite of the first surface. This invention produces a first surface 102 and the second surface 104 of different textures one from the other. One of the surfaces 102 has a texture that is smooth while the opposite surface 104 has a non-smooth texture with a knurled pattern. The elongated member preferably has side edges 110 that are of equal length and are spaced apart consistently that extend from the first end 106 to the second end 108.

The knurled pattern of surface 104 may be any suitable pattern providing a gripping texture. In one example, the knurled pattern may be a crossed pattern with a pitch (distance between protrusions) between 0.1 mm and 1 mm.

Figure 3:
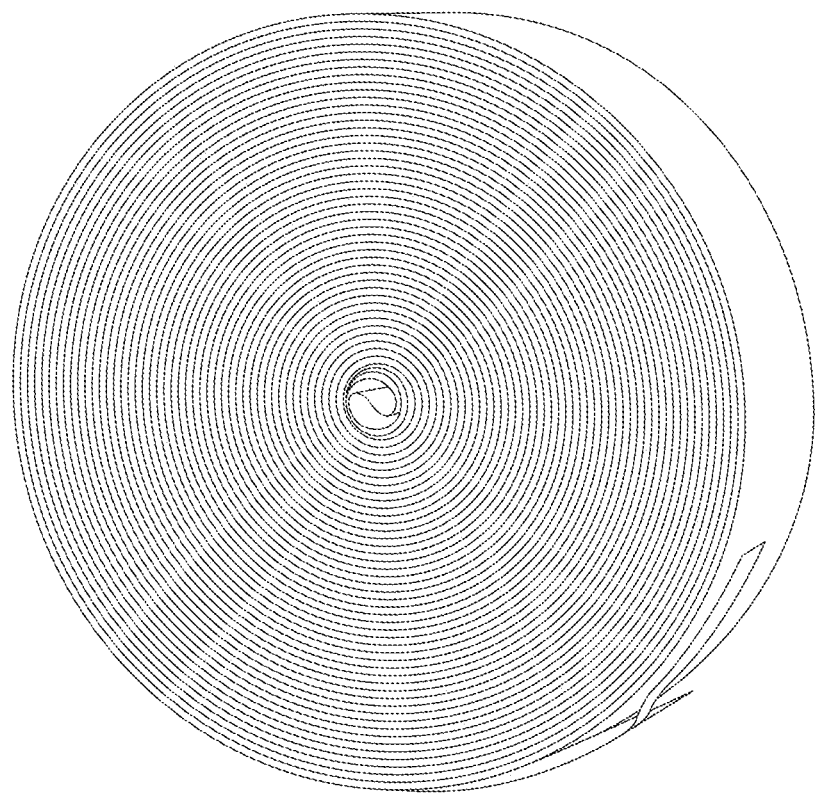
FIG. 3 illustrates a bilateral reversible disposable venous tourniquet band with textured and smooth sides in a large roll configuration, according to an example embodiment.
Figure 4:
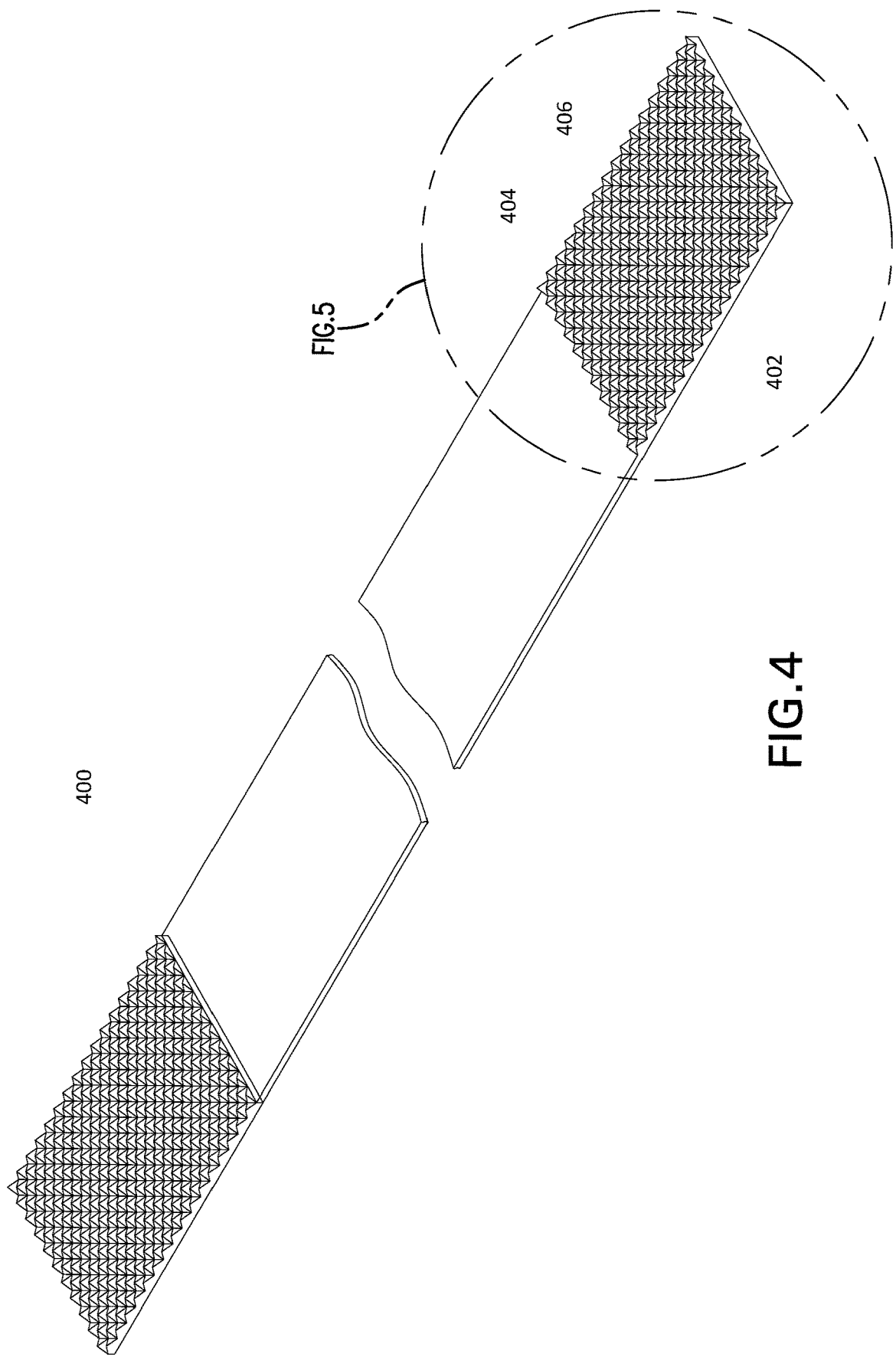
FIG. 4 illustrates a perspective view depicting a bilateral reversible disposable venous tourniquet band having a knurled crossed pattern, in accordance with embodiments of the present invention.

Tourniquet band 100 may have any suitable length and width for disposable use in a clinical setting. In particular embodiments, tourniquet band 100 may have any thickness between approximately 0.5 mm and 2 mm, and a length of approximately 18 inches. Tourniquet band 100 may be configured in any suitable manner for transportation and storage. For example, multiple tourniquet band 100 may be laid flat for transportation in a box, or rolled into individual reels. In particular embodiments, tourniquet band 100 may have a length of several feet and may be configured in a large roll that can be cut to a desired size at the time of use, as illustrated in FIG. 3.

Figure 5:
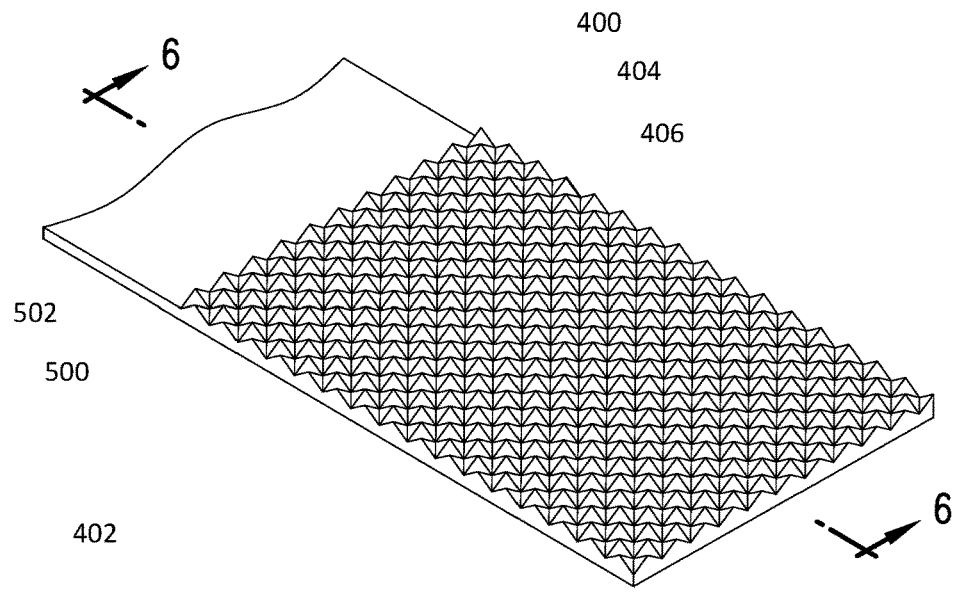
FIG. 5 illustrates a perspective view depicting an end of a bilateral reversible disposable venous tourniquet band having a knurled crossed pattern, in accordance with embodiments of the present invention.
Figure 6A:
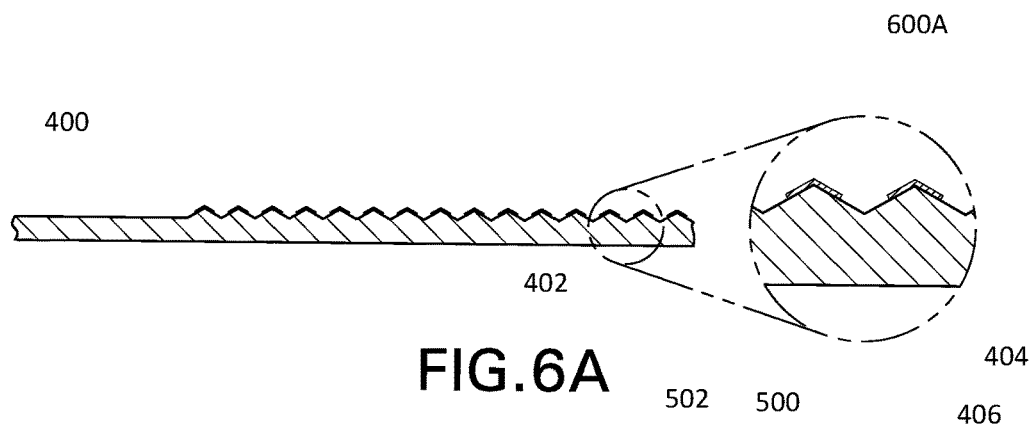
FIG. 6A illustrates a side cut-away view depicting a bilateral reversible disposable venous tourniquet band having a knurled crossed pattern with a plurality of protrusions and recesses, at least a portion of the plurality of protrusions having a layer of phosphorescent material at a distal portion, in accordance with embodiments of the present invention.
Figure 6B:
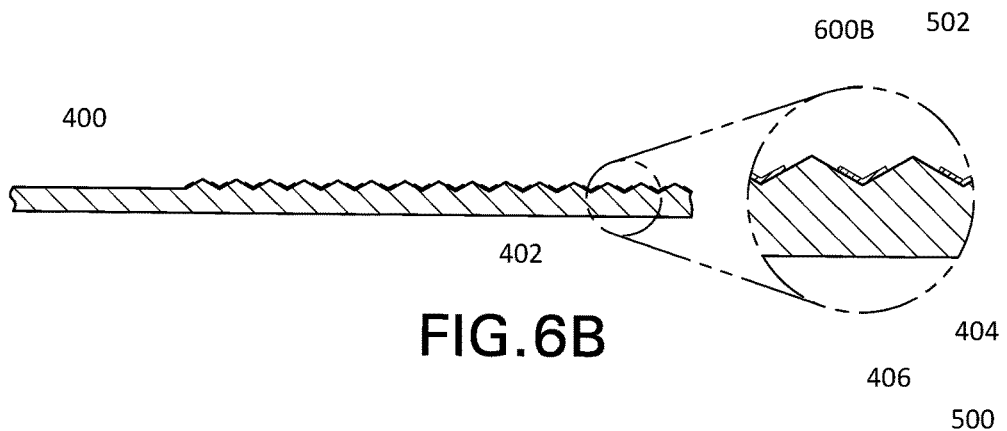
FIG. 6B illustrates a side cut-away view depicting a bilateral reversible disposable venous tourniquet band having a knurled crossed pattern with a plurality of protrusions and recesses, at least a portion of the plurality of recesses having a layer of phosphorescent material, in accordance with embodiments of the present invention.

FIGS. 4, 5, 6A, and 6B illustrate bilateral reversible disposable venous tourniquet band 400 having a knurled crossed pattern of a plurality of protrusions 404 and recesses 406. In these embodiments, at least a portion and/or end portion 402 of bilateral reversible disposable venous tourniquet band 400 has a knurled crossed pattern. Protrusion 404 of knurled crossed pattern is substantially pyramidal in shape and has a tapered configuration to aid in a user gripping bilateral reversible disposable venous tourniquet band 400. FIGS. 5, 6A, and 6B best illustrate protrusion 404 having base 500 of protrusion 404 having an outer perimeter edge greater in size than tip 502 of protrusion 404, thereby forming a tapered configuration. A first protrusion is oriented next to and/or adjacent to a second and/or a subsequent protrusion, forming a recess. In particular, the base 500 of first protrusion 404 shares the same border with the base of a second protrusion, thereby forming recess 406. This improved knurled crossed pattern is configured to retain a phosphorescent material to end portion 402 of bilateral reversible disposable venous tourniquet band 400 that receives heavy contact with the grip of a user during use. Base 500 of protrusion 404 of knurled crossed pattern is proximal or closest to bilateral reversible disposable venous tourniquet band 400. Tip 502 of protrusion 404 of knurled crossed pattern is the most distal portion or furthest portion away bilateral reversible disposable venous tourniquet band 400.

FIG. 6A illustrates bilateral reversible disposable venous tourniquet band 400 having a knurled crossed pattern with a plurality of protrusions 404 and recesses 406. At least a portion of plurality of protrusions 404 having layer of phosphorescent material 600A located thereon. In an embodiment, phosphorescent material 600A may be located at tip 502 of protrusion 404 of knurled cross pattern. It is within the scope of this invention for a phosphorescent material to be located on each end portion 402 of the knurled cross pattern of bilateral reversible disposable venous tourniquet band 400. In an example, the illuminated phosphorescent material 600A and/or 600B may be visible on the tied ribbon of a user's limb such, as an arm, when the tourniquet is tied around a limb of a patient. The location of the knurled crossed pattern in combination with a phosphorescent material being located at an end 402 of bilateral reversible disposable venous tourniquet band 400 is significant in that when bilateral reversible disposable venous tourniquet band 400 is tied and forms a ribbon during use, the end portions 402 will have a high probability and likelihood of be exposed to a user for the physical gripping and visual illumination.

It is within the scope of this invention for bilateral reversible disposable venous tourniquet band 400 having the phosphorescent material 600A being located on tip 502 of protrusions 404 of the knurled cross pattern as shown in FIG. 6A.

It is within the scope of this invention for bilateral reversible disposable venous tourniquet band 400 having the phosphorescent material 600B being located on recess 406 located at base 500 of protrusion 404 of the knurled crossed pattern as shown in FIG. 6B. When a layer of phosphorescent material 600B is located at a proximal location such as at recess 406 and/or base 500, it may not deteriorate as quickly as when a layer of phosphorescent material 600A is located at a distal location of the protrusion 404. For example, when a user grasps the knurled crossed pattern of bilateral reversible disposable venous tourniquet band 400, a distal portion and/or tip 502 of protrusion 404 of the knurled crossed pattern is highly exposed to the grasp of a user and any surface coatings such as, a layer of phosphorescent material, may rub off with a higher probability at a distal portion compared to a proximal location. When the phosphorescent material 600B is positioned within recess 406 of knurled crossed pattern, tip 502 of protrusion 404 forms a barrier that reduces a user's contact with layer of phosphorescent material 600B, thereby, prolonging the life of layer of phosphorescent material 600B being retained within recess 406 of knurled crossed pattern before being degraded from user contact during use.

It is within the scope of this invention for bilateral reversible disposable venous tourniquet band 400 having the phosphorescent material being located at and/or covering al least a portion of knurled cross pattern.

FIG. 6B illustrates bilateral reversible disposable venous tourniquet band 400 having end portion 402 with a knurled crossed pattern of a plurality of protrusions 404 and recesses 406. At least a portion of the plurality of recesses 406 have a layer of phosphorescent material 600B connected thereto.

It is to be appreciated that the Detailed Description section in addition to the Summary and Abstract sections, is intended to be used to interpret the claims. The Summary and Abstract sections may set forth one or more but not all exemplary embodiments of the invention as contemplated by the inventor(s), and thus, are not intended to limit the invention or the appended claims in any way.

While the invention has been described herein with reference to exemplary embodiments for exemplary fields and applications, it should be understood that the invention is not limited thereto. Other embodiments and modifications thereto are possible, and are within the scope and spirit of the invention. Further, embodiments (whether or not explicitly described herein) have significant utility to fields and applications beyond the examples described herein.

References herein to "one embodiment," "an embodiment," "an example embodiment," or similar phrases, indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of persons skilled in the relevant art(s) to incorporate such feature, structure, or characteristic into other embodiments whether or not explicitly mentioned or described herein.

The breadth and scope of the invention should not be limited by any of the above-described exemplary embodiments, but should be defined only in accordance with the following claims and their equivalents.

Now that the invention has been described,

What is claimed is:

1. A bilateral reversible disposable tourniquet band comprising:
   an elongated member having a flat structure, the elongated member comprised of a thermoplastic elastomer material, the elongated member comprising:
   a first surface having a smooth texture; and
   a second surface having a non-smooth texture comprising a knurled crossed pattern, the second surface being opposite the first surface, the knurled crossed pattern comprising a pattern of protrusions and recesses comprising rows of repeating pyramidal shapes having a tapered configuration, at least one protrusion of the pattern of protrusions having a phosphorescent material.

2. The bilateral reversible disposable tourniquet band of claim 1, wherein the knurled crossed pattern comprises a crossed pattern with a pitch between protrusions of between 0.1 mm and 1 mm.

3. The bilateral reversible disposable tourniquet band of claim 1, wherein the bilateral reversible disposable tourniquet band is packaged as a multiple tourniquet band reel.

4. The bilateral reversible disposable tourniquet band of claim 1, wherein the bilateral reversible disposable tourniquet band is packaged flat for transportation in a box.

5. The bilateral reversible disposable tourniquet band of claim 1, wherein the bilateral reversible disposable tourniquet band has a length of approximately 18 inches.

6. The bilateral reversible disposable tourniquet band of claim 1, wherein the bilateral reversible disposable tourniquet band includes a colorant added to the thermoplastic elastomer material.

7. The bilateral reversible disposable tourniquet band of claim 1, wherein the phosphorescent material is integrally formed within the knurled crossed pattern.

8. The bilateral reversible disposable tourniquet band of claim 1, wherein the phosphorescent material overlays a distal portion of at least one protrusion of the pattern of protrusions of the knurled crossed pattern.

9. The bilateral reversible disposable tourniquet band of claim 1, wherein the phosphorescent material overlays the recesses of the knurled crossed pattern.

10. The bilateral reversible disposable tourniquet band of claim 9, wherein the phosphorescent material does not overlay a distal portion of at least one protrusion of the pattern of protrusions of the knurled crossed pattern.

11. A bilateral reversible disposable tourniquet band comprising:
    an elongated member having a flat structure, the elongated member comprised of a thermoplastic elastomer material, the elongated member comprising:
    a first surface having a smooth texture, and
    a second surface, at least a portion of the second surface having a non-smooth texture comprising a knurled crossed pattern, the second surface being located opposite the first surface, the knurled crossed pattern comprising a pattern of protrusions comprising rows of repeating pyramidal shapes having a tapered configuration, a first protrusion of the pattern of protrusions is oriented adjacent to a second protrusion thereby forming a recess, at least a portion of the knurled crossed pattern being a phosphorescent material.

12. The bilateral reversible disposable tourniquet band of claim 11, wherein the knurled crossed pattern comprises a pitch between protrusions of between 0.1 mm and 1 mm.

13. The bilateral reversible disposable tourniquet band of claim 11, wherein the phosphorescent material is integrally formed within the knurled crossed pattern.

14. The bilateral reversible disposable tourniquet band of claim 11, wherein the phosphorescent material overlays a tip of the first protrusion of the pattern of protrusions of the knurled crossed pattern.

15. The bilateral reversible disposable tourniquet band of claim 11, wherein the phosphorescent material overlays the recess of the knurled crossed pattern.

16. The bilateral reversible disposable tourniquet band of claim 15, wherein the phosphorescent material does not overlay a tip of the first protrusion of the pattern of protrusions of the knurled crossed pattern.

17. The bilateral reversible disposable tourniquet band of claim 11, wherein the bilateral reversible disposable tourniquet band includes a colorant added to the thermoplastic elastomer material.

* * * * *